United States Patent [19]

Kikumoto et al.

[11] Patent Number: 4,764,618
[45] Date of Patent: Aug. 16, 1988

[54] ARGININE DERIVATIVES AND PHARMACEUTICALLY ACCEPTABLE ACID ADDITION SALTS THEREOF

[75] Inventors: Ryoji Kikumoto; Yoshikuni Tamao, both of Tokyo; Shinji Tonomura; Akira Maruyama, both of Yokohama; Shosuke Okamoto; Akiko Okunomiya, both of Kobe, all of Japan

[73] Assignee: Mitsubishi Chemical Industries Limited, Tokyo, Japan

[21] Appl. No.: 65,156

[22] Filed: Jun. 19, 1987

Related U.S. Application Data

[63] Continuation of Ser. No. 696,532, Jan. 30, 1985, abandoned.

[30] Foreign Application Priority Data

Feb. 6, 1984 [JP] Japan .................. 59-19800

[51] Int. Cl.[4] .......................................... C07D 405/12
[52] U.S. Cl. ..................................... 546/196; 546/205; 546/206
[58] Field of Search .................. 546/196, 205, 206

[56] References Cited

U.S. PATENT DOCUMENTS 4,066,773  1/1977  Okamoto ........................... 546/196
4,073,914  2/1978  Kikumoto ......................... 546/206

OTHER PUBLICATIONS

Nesheim, "Biochemistry" 18(6), pp. 996-1003 (1979).
Kikumoto-II, "J. Med. Chem." (23), pp. 1293-1299 (1980).

*Primary Examiner*—Robert J. Warden
*Assistant Examiner*—Robert Benson
*Attorney, Agent, or Firm*—Oblon, Fisher, Spivak, McClelland & Maier

[57] ABSTRACT

Novel arginine derivatives represented by the general formula

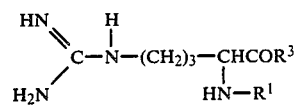

wherein $R^1$ stands for a naphthalenesulfonyl, a naphthalenecarbonyl, a 1,2,3,4-tetrahydronaphthalenesulfonyl, a 1,2,3,4-tetrahydronaphthalenecarbonyl, a dioxa b-6,7-naphthalenesulfonyl, a dioxa b-6,7-naphthalenecarbonyl, a 1,2,3,4-tetrahydro-8-quinolinesulfonyl, a 1,2,3,4-tetrahydro-8-quinolinecarbonyl, a dibenzofuransulfonyl, a dibenzofurancarbonyl, a fluorenesulfonyl, a fluorenecarbonyl, a dibenzothiophenesulfonyl or a dibenzothiophene, and $R^2$ stands for a piperidino or a piperazino are disclosed. These arginine derivatives and their pharmaceutically acceptable salts have trypsin-inhibiting activity and useful as a pancreatitis remedy.

4 Claims, No Drawings

ARGININE DERIVATIVES AND PHARMACEUTICALLY ACCEPTABLE ACID ADDITION SALTS THEREOF

This application is a continuation of application Ser. No. 696,532, filed on Jan. 30, 1985, now abandoned.

TECHNICAL FIELD OF THE INVENTION

This invention relates to arginine derivatives and acid addition salts thereof.

BACKGROUND OF THE INVENTION

Pancreaitis is thought to be caused by activation of trypsin in pancreas, activation of various kinds of protease triggered by the trypsin activation and the resulting autodigestion of the pancreas tissue. Therefore, a trypsin-inhibitor is considered useful as a remedy for pancreaitis which prevents occurrence and development of pancreaitis.

We made a research in search of compounds having strong anti-trypsin activity and have found that certain arginine derivatives and acid addition salts thereof have such anti-trypsin activity, and thus have reached this invention.

SUMMARY OF THE INVENTION

The present invention provides arginine derivatives represented by the general formula (I)

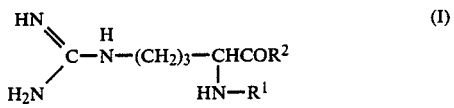

wherein $R^1$ stands for

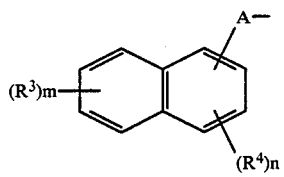

wherein $R^3$ and $R^4$ stand for hydroxyl group, cyano group, halogen atom, alkyl group, alkoxyl group, acyl group, halogen-substituted alkyl group, carboxyl group or alkoxycarbonyl group, m is an integer of 0~4, n is an integer of 0~3, and when m and/or n is not less than 2, $R^3$'s in $(R^3)$m and/or $R^4$'s in $(R^4)$n may respectively be different, and A stands for —$SO_2$— or —CO—;

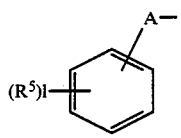

wherein $R^5$ stands for hydroxyl group, cyano group, halogen atom, alkyl group, alkoxy group, acyl group, halogen-substituted alkyl group, carboxyl group or alkoxycarbonyl group, l is an integer of 0~5, and when l is not less than 2, $R^5$'s in $(R^5)$l may be different, and A stands for —$SO_2$— or —CO—;

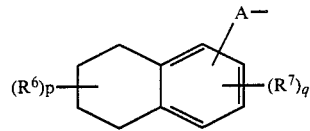

wherein $R^6$ and $R^7$ stand for hydroxyl group, cyano group, halogen atom, alkyl group, alkoxy group, acyl group, halogen-substituted alkyl group, carboxyl group or alkoxycarbonyl group, p is an integer of 0~4, q is an integer of 0~3, and when p and/or q is not less than 2, $R^6$'s in $(R^6)$p and/or $R^7$'s in $(R^7)$q may respectively be different, and A stands for —$SO_2$— or —CO—;

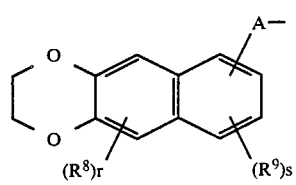

wherein $R^8$ and $R^9$ stand for hydroxyl group, cyano group, halogen atom, alkyl group, alkoxy group, acyl group, halogen-substituted alkyl group, carboxyl group or alkoxycarbonyl group, r is an integer of 0~2, s is an integer of 0~3, and when r and/or s is not less than 2, $R^8$'s in $(R^8)$r and/or $R^9$'s in $(R^9)$s may be different, and A is —$SO_2$— or —CO—;

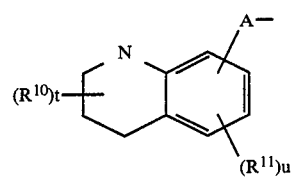

wherein $R^{10}$ and $R^{11}$ stand for hydroxyl group, cyano group, halogen atom, alkyl group, alkoxy group, acyl group, halogen-substituted alkyl group, carboxyl group or alkoxycarbonyl group, t and u are an integer of 0~3, and when t and/or u is not less than 2, $R^{10}$'s in $(R^{10})$t and/or $R^{11}$'s in $(R^{11})$u may respectively be different, and A stands for —$SO_2$— or —CO—; or

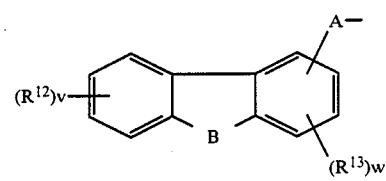

wherein $R^{12}$ and $R^{13}$ stand for hydroxyl group, acyl group, halogen atom, alkyl group, alkoxy group, cyano group, halogen-substituted alkyl group, carboxyl group or alkoxycarbonyl group, v is an integer of 0~4, w is an integer of 0~3, and when v and/or w is not less than 2, $R^{12}$'s in $(R^{12})$v and/or $R^{13}$'s in $(R^{13})$w may respectively be different, A stands for —$SO_2$— or —CO—, and B stands for —$CH_2$—, —O— or —S—; and $R^2$ stands for

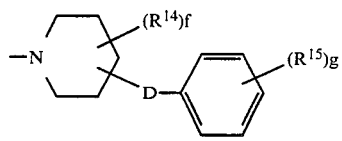

wherein $R^{14}$ and $R^{15}$ stand for hydroxyl group, cyano group, halogen atom, alkyl group, alkoxy group, acyl group, halogen-substituted alkyl group, carboxyl group or alkoxycarbonyl group, f is an integer of 0~4, g is an integer of 0~3, and when f and/or g is not less than 2, $R^{14}$'s in $(R^{14})f$ and/or $R^{15}$'s in $(R^{15})g$ may respectively be different, and D stands for —O—, —S—, —CONH— or —(CH$_2$)h—, wherein h is an integer of 0~4; or

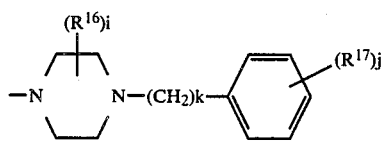

wherein $R^{16}$ and $R^{17}$ stand for hydroxyl group, cyano group, halogen atom, alkyl group, alkoxy group, acyl group, halogen-substituted alkyl group, carboxyl group or alkoxycarbonyl group, i is an integer of 0~4, j is an integer of 0~3, and when i and/or j is not less than 2, $R^{16}$'s in $(R^{16})i$ and/or $R^{17}$'s in $(R^{17})j$ may respectively be different, and k is an integer of 0~4; and pharmaceutically acceptable acid addition salts thereof.

DETAILED DESCRIPTION OF THE INVENTION

Now the invention will be specifically described in detail.

The arginine derivatives of this invention are represented by the general formula (I)

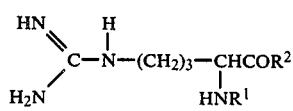

In this formula, $R^1$ stands for the previously indicated formulas 1~6, and $R^2$ stands for the previously indicated formulas a or b.

In the formulas 1~6 and a~b, A stands for —SO$_2$— or —CO—, and specific examples of $R^3 \sim R^{17}$ are hydroxyl group; cyano group; halogen atom such as fluorine, chlorine, bromine, iodine, etc.; C$_1$~C$_6$ alkyl group such as methyl, ethyl, propyl, butyl, pentyl, hexyl, etc.; C$_1$~C$_6$ alkoxy group such as methoxy, ethoxy, propoxy, butoxy, pentyloxy, hexyloxy, etc., C$_2$~C$_6$ acyl group such as acetyl, propionyl, butyryl, valeryl, hexanoyl, etc.; halogen-substituted C$_1$~C$_6$ alkyl group such as trifluoromethyl, chloromethyl, 2-chloroethyl, 2-bromoethyl, 2-chloropropyl, 3-chloropropyl, 2-chlorobutyl, 4-chlorobutyl, etc.; carboxyl group; C$_2$~C$_6$ alkoxycarbonyl such as methoxycarbonyl, ethoxycarbonyl, propoxycarbonyl, butoxycarbonyl, etc.; etc.

The positions of the substituents A and $R^3 \sim R^{17}$ are not specifically restricted.

Preffered examples of $R^1$ are:

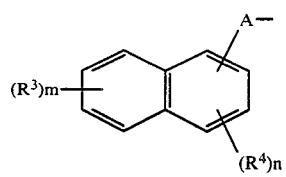

wherein $R^3$ stands for hydroxyl group, halogen, preferably chlorine atom, C$_1$~C$_6$, preferably C$_1$~C$_4$ alkyl group, C$_1$~C$_6$, preferably C$_2$~C$_4$ alkoxy group, carboxyl group, or C$_2$~C$_6$, preferably C$_2$~C$_4$ alkoxycarbonyl group; $R^4$ stands for C$_1$~C$_6$, preferably C$_1$~C$_4$ alkoxy group, m is an integer of 0~2, n is an integer of 0 or 1, and when m is 2, the two $R^3$'s may be different, and A stands for —SO$_2$— or —CO—.

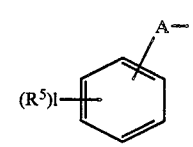

Wherein $R^5$ stands for C$_1$~C$_6$, preferably C$_1$~C$_4$ alkyl group or C$_1$~C$_6$, preferably C$_1$~C$_4$ alkoxy group, l is an integer of 0~3, and when l not less than 2, $R^5$'s in $(R^5)l$ may be different, and A stands for —SO$_2$— or —CO—;

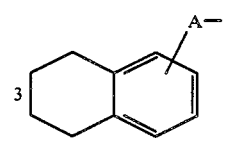

wherein A stands for —SO$_2$— or —CO—, preferably —SO$_2$—;

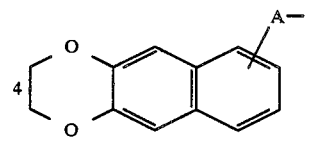

wherein A stands for —SO$_2$— or —CO—, preferably —SO$_2$—;

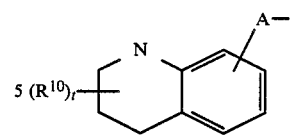

wherein $R^{10}$ stands for C$_1$~C$_6$, preferably C$_1$~C$_4$ alkyl group, t is 0 or 1, and A stands for —SO$_2$— or —CO—, preferably —SO$_2$—; or

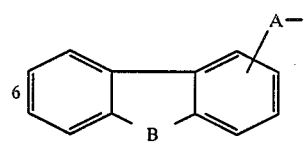

wherein A stands for —SO$_2$— or —CO—, preferably —SO$_2$—, and B stands for —CH$_2$— or —O—.

Preferred examples of R$^2$ are:

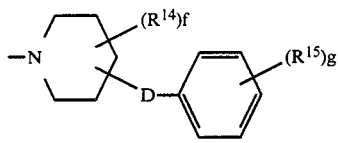
a wherein R$^{14}$ stands for cyano group, C$_2$~C$_6$, preferably C$_2$~C$_4$ acyl group, carboxyl group, or C$_2$~C$_6$, preferably C$_2$~C$_4$ alkoxycarbonyl group, R$^{15}$ stands for halogen atom, C$_1$~C$_6$, preferably C$_1$~C$_4$ alkyl group, C$_1$~C$_6$, preferably C$_2$~C$_4$ alkoxy group, carboxyl group, C$_2$~C$_6$, preferably C$_2$~C$_4$ alkoxycarbonyl group, f is 0 or 1, g is an integer of 0~2, and when g is 2, the two R$^{15}$'s may be different, and D stands for —O—, —CONH— or —(CH$_2$)h—, wherein h is 0 or 1; and

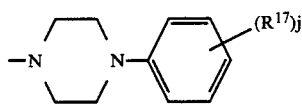
b wherein R$^{17}$ stands for hydroxyl group, halogen atom, C$_1$~C$_6$, preferably C$_1$~C$_4$ alkyl group, C$^1$~C$_6$, preferably C$_1$~C$_4$ alkoxy group, halogen-substituted C$_1$~C$_6$, preferably C$_1$~C$_4$ alkyl group, j is an integer of 0~2, and when j is 2, the two R$^{17}$'s may be different.

Typical examples of the arginine derivative of this invention are:
1-[N$^2$-(7-methoxy-2-naphthalenesulfonyl)-L-arginyl]-4-phenylpiperidine,
1-[N$^2$-(7-methoxy-2-naphthalenesulfonyl)-L-arginyl]-4-phenyl-2-piperidinecarboxylic acid,
1-[N$^2$-(7-methoxy-2-naphthalenesulfonyl)-L-arginyl]-4-(2-chlorophenyl)-piperazine,
1-[N$^2$-(7-methoxy-2-naphthalenesulfonyl)-L-arginyl]-4-phenylpiperazine,
1-[N$^2$-(7-methyl-2-naphthalenesulfonyl)-L-arginyl]-4-phenylpiperidine,
1-[N$^2$-(7-ethoxy-2-naphthalenesulfonyl)-L-arginyl]-4-phenylpiperadine,
1-[N$^2$-(7-methoxy-2-naphthalenesulfonyl)-L-arginyl]-4-(3-methylphenyl)-piperidine, etc.

Pharmaceutically acceptable acid addition salts of the above described compounds are also included in the scope of this invention.

In the arginine derivatives of this invention, when the carbon atom in the piperidine ring or the piperazine ring to which a carboxyl group or alkoxycarbonyl group is attached is asymmetric, there exisit two optically active isomers, that is, D- and L-diastereomer as well as a racemic body or DL-mixture. These are also included in the scope of this invention.

The above-mentioned compounds are listed only for exhibiting the diversity in structures of the compounds encompassed in this invention, and this invention is not limited to these specific compounds.

For the preparation of the arginine derivatives of this invention, various processes can be employable depending upon starting materials and/or intermediates to be employed. However, a few preferred processes are outlined below.

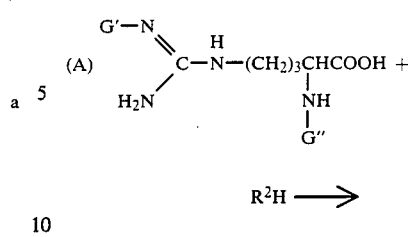
(A) (II)

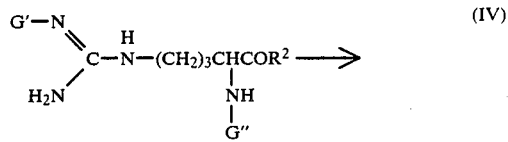
(III)

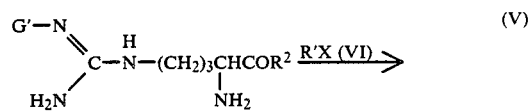
(IV)

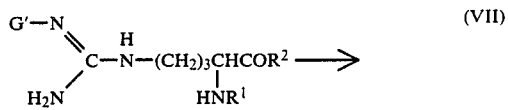
(V)

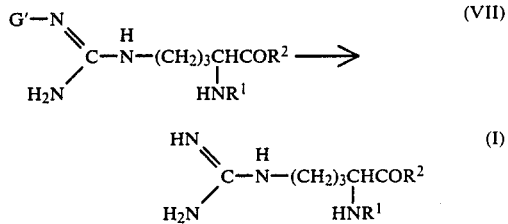
(VII)

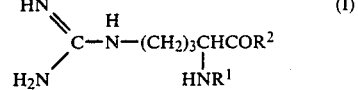
(I)

In the above chemical formulas, R$^1$ and R$^2$ are as defined above, X stands for halogen atom. G' stands for a protecting group for the guanidino group such as nitro, tosyl, trityl, etc. G" stands for a protecting group for the α-amino group such as benzyloxycarbonyl, t-butoxycarbonyl, etc.

The arginine derivative (I) is obtained by reacting an L-arginyl compound (II) of which the guanidino group and α-amino group are protected with a compound (III) to give an arginine derivative (IV), removing the protecting group of the α-amino group of the derivative (IV) by acid decomposition, etc., condensing the resulting compound (V) with a compound (VI), and finally removing the protecting group of the guanidino group by hydrogenation decomposition.

The reaction of the compound (II) and the compound (III) can be conducted by way of ordinary method, such as acid chloride method, acid azide method, mixed acid anhydride method, active ester method or carbodiimide method, although the mixed acid anhydride method using a base such as triethylamine and a condensation reagent such as isobutyl chloroformic acid is preferred.

The condensation is usually carried out in the presence of a base such as triethylamine, potassium carbonate, etc. in a suitable solvent. The reaction can be conducted in a temperature range of from 0° C. to the boiling temperature of the used solvent for 10 minutes to 15 hours.

Preferred organic solvents are ethers such as tetrahydrofuran, dioxane, etc.; alcohols such as methanol, ethanol, etc.; fatty acids such as acetic acid; esters such as ethyl acetate; hydrocarbons such as benzene; halogenated hydrocarbons such as chloroform, dichloromethane, etc.; and mixtures of these.

Acid decomposition is usually carried out by bringing the arginine derivative (IV) in contact with an excess amount of an acid such as hydrogen fluoride, hydrogen chloride, hydrogen bromide, trifluoroacetic acid, etc. in a solvent such as an alcohol, an ether, a fatty acid, an ester, a hydrocarbon, etc., or a mixture of these at a temperature of $-10° \sim 100°$ C., preferably at room temperature for 30 minutes to 24 hours.

Hydrogenation decomposition is usually carried out in the presence of a hydrogen-activating catalyst such as Raney nickel, palladium, platinum, etc. in a hydrogen atmosphere. Alcohols, ethers, fatty acids, esters, hydrocarbons or mixtures of these can be used as reaction media. The reaction is conducted at a temperature between 0° C. and the boiling temperature of the used solvent.

By distilling off the solvent after hydrogenation decomposition is finished, arginine derivative (I) is obtained.

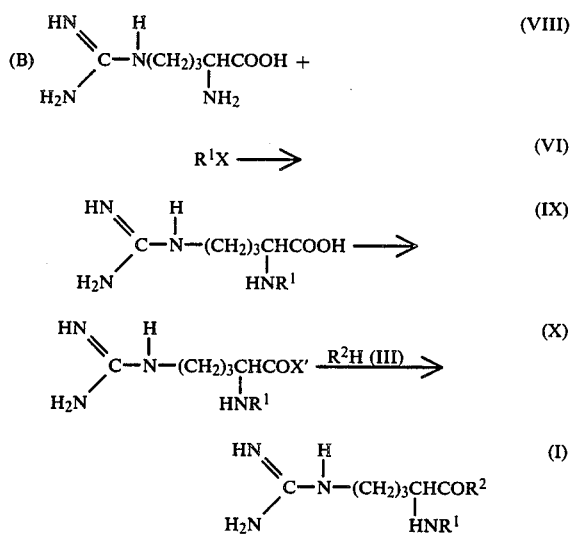

In the above chemical formulas, $R^1$ and $R^2$ and $X$ are as defined above, and $X'$ stands for halogen atom.

The arginine derivative (I) is obtained by condensing an L-arginine (VIII) with a compound (VI), halogenating the resulting compound (IX) using more than an equivalent amount of a halogenating agent such as thionyl chloride, phosphorus oxychloride, phosphorus trichloride, phosphorus pentachloride, phosphorus tribromide, etc., and finally condensing the resulting compound (X) with a compound (III).

Hologenation reaction can be conducted with or without a solvent, although hydrocarbons such as chloroform, dichloromethane, etc., ethers such as tetrahydrofuran, dioxane, etc. are preferably used.

Reaction temperature is between $-10°$ C. and room temperature. Reaction time is not critical, and is varied depending upon the used solvent and employed reaction temperature, although it is usually 15 minutes to 5 hours.

Condensation can be carried out in accordance with the steps described with respect to Process (A).

Of the compounds of this invention, the ester derivatives can be obtained by esterifying the carboxyl derivatives by the ordinary method. Also, carboxyl derivatives are obtained by hydrolysis or acid decomposition of ester derivatives. Conditions of the above-mentioned hydrolysis, and acid decomposition are well known among those skilled in the art.

The arginine derivatives in accordance with this invention form acid addition salts with various inorganic and organic acids.

The arginine derivatives obtained by the above described reactions are isolated as free bases or acid addition salts.

Further, pharmaceutically acceptable acid addition salts of the arginine derivatives can be obtained by reaction of a free base and an acid.

As acids therefor, hydrochloric acid, hydrobromic acid, hydriodic acid, nitric acid, sulfuric acid, phosphoric acid, acetic acid, citric acid, maleic acid, succinic acid, lactic acid, tartaric acid, gluconic acid, benzoic acid, methanesulfonic acid, ethanesulfonic acid, p-toluenesulfonic acid, etc. can be listed.

As mentioned above, the arginine derivatives and parmaceutically acceptable acid addition salts thereof in accordance with this invention have specific strong inhibiting activity against trypsin, and are useful as preventive and therapeutic agents for pancreaitis.

When the compounds of this invention are used as trypsin inhibitors, they can be administered in any form. However, the methods described below are preferably employed.

That is, parenteral administration such as subcutaneous injection, intravenous injection, intramuscular injection, intrapenitoneal injection, etc. as well as oral administration are employed.

Dose is determined by considering age of patient, health conditions, body weight, simultaneously employed treatment if any, frequency of treatment, nature of wanted effect, etc.

However, the usual dose is $0.5 \sim 50$ mg/kg weight, ordinarily $1 \sim 30$ mg/kg weight active ingredient per day, and the drug is administered once a day or more.

When orally administered, they are given in the form of tablet, capsule, powder, liquid, elixir, etc. When administered orally, they are given in the form of disinfected fluid such as solution or suspension. In these cases, non-toxic solid or liquid pharmaceutical adjuvant can be incorporated in the administrable preparation.

Ordinary gelatin capsule is an example of the solid administrable form. The active substance can be made into tablets or powder together with one or more adjuvants. Capsules, tablets and powder contain usually $5 \sim 95\%$, preferably $25 \sim 90\%$ of the active ingredient.

In these administrable forms, $5 \sim 500$ mg, preferably $25 \sim 250$ mg of the active ingredient is contained.

Water, or kerosene and mineral oil, or oils of animal and plant origin such as peanut oil, sesame oil, etc. as well as synthesized oils are used as liquid excipients.

As liquid excipient, physiological salt solution, solutions of dextrose and similar sugars, and glycols such as ethyleneglycol, propyleneglycol, polyethyleneglycol are preferred. In the case of injection liquid using physiological salt solution, $0.5 \sim 20\%$, preferably $1 \sim 10\%$ of the active ingredient is contained.

In the case of orally administered liquid preparations, suspension or syrup containing $0.5 \sim 10\%$ by weight of the active ingredient is preferred.

Now the invention will be specifically explained by way of working examples. However, the invention is not limited to such working examples only.

EXAMPLE 1

(a) 29.7 g (0.093 mole) of $N^2$-(tert-butoxycarbonyl)-$N^G$-nitro-L-arginine and 9.41 g (0.093 mole) of triethylamine are dissolved in 400 ml of tetrahydrofuran.

To this solution, 127 g (0.093 mole) of isobutyl chloroformate in 20 ml of tetrahydrofuran is added dropwise over a 5 minute period at $-25° \sim -20°$ C. After 30 minutes, a solution of 15.0 g (0.093 mole) of 4-phenylpiperidine in 50 ml of tetrahydrofuran is added dropwise at $-25° \sim -20°$ C. over 30 minutes. After 30 minutes, the reaction mixture is brought to room temperature, and the reaction is allowed to continue further for one hour. Thereafter, the solvent is distilled off, and the residue is dissolved in 400 ml of ethyl acetate. The solution is washed successively with water, a 10% aqueous solution of citric acid, saturated sodium hydrogen carbonate aqueous solution, and water, and is dried over anhydrous sodium sulfate. The residue is collected by distillation of the solvent and purified by column chromatography using 500 g silica gel. Impurities are first eluted with chloroform and then the object substance is eluted with a 3%-methanol/chloroform mixture. By distilling off the solvent of the fraction of the object compound, 33.8 g of 1-[$N^2$-(tert-butoxycarbonyl)-$N^G$-nitro-L-arginyl]4-phenylpiperidine is obtained as an amorphous solid. Yield 79%.

(b) 27.0 g (0.058 mole) of the 1-[$N^2$-(tert-butoxycarbonyl)-$N^G$-nitro-L-arginyl]-4-phenylpiperidine is dissolved in 100 ml of ethyl acetate, and 100 ml of a 20%-hydrochloric acid/ethyl acetate mixture is added to the solution under ice-chilling. After 10 minutes, the reaction mixture is brought to room temperature, and is further stirred for three hours. In the course of the reaction, a precipitate is formed. The precipitate is washed well by adding 200 ml of ethyl ether, and the solvent is removed by decantation. After this operation is repeated several times, the solvent is removed completely, and 22.8 g of 1-($N^G$-nitro-L-arginyl)-4-phenylpiperidine hydrochloride is obtained as a white powder. Yield 98%.

(c) 2.0 g (0.00501 mole) of the 1-($N^G$-nitro-L-arginyl)-4-phenylpiperidine hydrochloride and 1.52 g (0.015 mole) of triethylamine are dissolved in 50 ml of chloroform, and 1.41 g (0.00551 mole) of 7-methoxy-2-naphthalenesulfonyl chloride is added to the solution under ice chilling. After 10 minutes, the reaction mixture is brought to room temperature, and the reaction is allowed to continue further for 2 hours. The reaction mixture is washed successively with 1N hydrochloric acid, water, saturated aqueous solution of sodium hydrogen carbonate and water, and is dried over anhydrous sodium sulfate. The solvent is distilled off and the residue is purified by column chromatography using 35 g of silica gel. The remaining unreacted acid chloride is eluted with chloroform, and the object substance is eluted with 3%-methanol/chloroform solution. The solvent of the object substance fraction is distilled off, and 1.91 g of 1-[$N^2$-(7-methoxy-2-naphthalenesulfonyl)-$N_G$-nitro-L-arginyl]-4-phenylpiperidine is obtained as an amorphous solid. Yield 65%.

(d) 1.91 g of the 1-[$N^2$-(methoxy-2-naphthalenesulfonyl)-$N^G$-nitro-L-arginyl]-4-phenylpiperidine is dissolved in a mixed solution of 150 ml methanol, 150 ml water, and 1.5 ml acetic acid, and is subjected to hydrogenation with 400 g palladium black added at $30° \sim 35°$ C. under ordinary pressure. After 20 hours, the catalyst is separated by filtration, and the solvent is distilled off until 100 ml remains. Addition of 2N sodium hydroxide solution to pH 11 causes precipitation of crystals. These crystals are collected by filtration, washed with water and dried, and 1.56 g of 1-[$N^2$-(7-methoxy-2-naphthalenesulfonyl)-L-arginyl]-4-phenylpiperidine is obtained. Yield 89%. m.p. $217° \sim 220°$ C. (decomp.) IR(KBr): 3340, 1620, 1450 cm$^{-1}$.

EXAMPLE 2

(a) 10.94 g (0.0343 mole) of $N^2$-(tert-butoxycarbonyl)-$N^G$-nitro-L-arginine and 3.47 g (0.0343 mole) of triethylamine are dissolved in 140 ml of tetrahydrofuran, and 4.69 g (0.0343 mole) of isobutyl chloroformate in 10 ml of tetrahydrofuran is added dropwise over 10 minutes at $-25° \sim -20°$ C. After the reaction mixture is allowed to stand for 30 minutes, a solution of 8.0 g (0.03430 mole) ethyl 4-phenyl-2-piperidinecarboxylate in 15 ml tetrahydrofuran is added to the reaction mixture dropwise over a 15 minute period at $-25° \sim -20°$ C. The reaction is allowed to continue for 30 minutes, and further for one hour at room temperature. Thereafter, the solvent is distilled off, and the residue is dissolved in 150 ml ethyl acetate. Thereafter, the product is treated in the same way as described in Example 1 (a), and 8.71 g of the object compound, ethyl 1-[$N^2$-(tert-butoxycarbonyl)-$N^G$-nitro-L-arginyl]-4-phenyl-2-piperidinecarboxylate is obtained as an amorphous solid. Yield 48%.

(b) 8.71 g of the ethyl 1-[$N^2$-(tert-butoxycarbonyl)-$N^G$-nitro-L-arginyl]-4-phenyl-2-piperidinecarboxylate is dissolved in 35 ml of ethyl acetate, and 35 ml of a 20%-hydrochloric acid/ethyl acetate mixture is added to the solution under ice chilling. After 10 minutes, the reaction mixture is brought to room temperature, and is allowed to react further for 3 hours. In the course of the reaction, a precipitate is formed. The precipitate is washed well by adding 80 ml of ethyl ether, and the solvent is removed by decantation. This operation is repeated several times, and the solvent is completely distilled off. Thus 6.0 g of white powder of ethyl 1-($N^G$-nitro-L-arginyl)-4-phenyl-2-piperidinecarboxylate hydrochloric acid salt is obtained. Yield 79%.

(c) 2.0 g (0.00398 mole) of the ethyl 1-($N^G$-nitro-L-argininyl-4-phenyl-2-piperidinecarboxylate hydrochloric acid salt and 1.21 g (0.0119 mole) of triethylamine are dissolved in 50 ml of chloroform. To the solution, 1.12 g (0.00438 mole) of 7-methoxy-2-naphthalenesulfonyl chloride is added under ice chilling. After 10 minutes, the reaction mixture is brought to room temperature and the reaction is allowed to continue further for 2 hours. The reaction mixture is treated and the object compound is purified by column chromatography in the same way as described in Example 1 (c), and 2.57 g of the object compound, ethyl 1-[$N^2$-(7-methoxy-2-naphthalenesulfonyl)-$N^G$-nitro-L-arginyl]-4-phenyl-2-piperidinecarboxylate is obtained as an amorphous solid. Yield 94%.

(d) 1.66 g of the ethyl 1-[$N^2$-(methoxy-2-naphthalenesulfonyl)-$N^G$-nitro-L-arginyl]-4-phenyl-2-piperidinecarboxylate is dissolved in a mixture of 12 ml acetic acid and 100 ml methanol, and 200 mg palladium black is added to the solution. Thus hydrogenation is conducted under ordinary pressure. After 25 hours, the catalyst is removed by filtration, and the solvent is distilled off. The residue is dissolved in 20 ml of ethanol, and is subjected to hydrolysis by addition of 12 ml 1N sodium hydroxide aqueous solution for 10 hours. The reaction mixture is neutralized with 1N hydrochloric acid, and the solvent is distilled off to a half in volume. Crystals deposit, which are collected by filtration, washed with water and dried. Thus 1.18 g of 1-[$N^2$-(7-methoxy-2-naphthalenesulfonyl)-L-arginyl]-4-phenyl-2-piperidinecarboxylic acid is obtained. Yield 84%. m.p. $183° \sim 186°$ C. IR(KBr): 3400, 1620, 1595 cm$^{-1}$.

EXAMPLE 3

(a) 12.2 g (0.0701 mole) of L-arginine and 10.7 g (0.0771 mole) of potassium carbonate are dissolved in 90 ml water, and a solution of 15.0 g (0.0584 mole) of 7-methoxy-2-naphthalenesulfonyl chloride in 120 ml benzene is added to the solution, and the mixture is stirred at room temperature. After 10 hours, the deposited crystals are collected by filtration, washed with benzene and water, and dried. Thus 6.63 g of $N^2$-(7-methoxy-2-naphthalenesulfonyl)-L-arginine 6.63 g is obtained. Yield 29%. m.p. 190°~192° C.

(b) To 2 g (0.0051 mole) of $N^2$-(7-methoxy-2-naphthalenesulfonyl)-L-arginine, 10.7 ml of thionyl chloride and 2 drops of dimethylformamide are added and the mixture is vigorously agitated for 2.5 hours at 30° C. Thus a homogeneous solution is obtained. 50 ml of ethyl ether is added to the solution and the solution is further vigorously agitated and the supernatant is removed by decantation. This operation is repeated several times and finally the solvent is completely removed. Thus 2.4 g of a yellow powder of $N^2$-(7-methoxy-2-naphthalenesulfonyl)-L-argininy chloride is obtained.

The thus obtained $N^2$-(7-methoxy-2-naphthalene-sulfonyl)-L-arginyl chloride (2.4 g) is immediately added to a solution of 1.64 g (0.00608 mole) 1-(2-chlorophenyl)piperazine dihydrochloride and 2.56 g (0.0253 mole) triethylamine in 50 ml chloroform under ice chilling. After 10 minutes, the mixture is brought to room temperature, and allowed to stand overnight. Then the reaction mixture is washed with water and the solvent is distilled off. The residue is washed with ethyl ether and dissolved in a 30%-ethanol/50 ml water mixture, and made basic with a 2N sodium hydroxide aqueous solution to pH 10. Thus an oily substance is deposited and is crystallized on standing. The crystals are collected by filtration, dried, and recrystallized from 20 ml THF, and 0.83 g of 1-[$N^2$-(7-methoxy-2-naphthalenesulfonyl)-L-arginyl]-4-(2-chlorophenyl)piperazine is obtained. Yield 28%. m.p. 219°~221° C. (decomp.) IR(KBr): 3330, 1625, 1480 cm$^{-1}$.

EXAMPLE 4

(a) 2.0 g (5.01 mmoles) of the 1-($N^G$-nitro-L-arginyl)-4-phenylpiperidine hydrochloride obtained in Example 1 (b) and 1.52 g (15.03 mmoles) of triethylamine are dissolved in 50 ml of chloroform, and 1.33 g (5.51 mmoles) of 3-methyl-8-quinolinesulfonyl chloride is added to the solution under ice chilling. After 10 minutes, the reaction mixture is brought to room temperature and the reaction is allowed to continue for 2 hours. Then the reaction mixture is washed successively with 0.5N hydrochloric acid, water, saturated sodium hydrogen carbonate aqueous solution, and water, and dried over anhydrous sodium sulfate. The solvent is distilled off and the residue is purified by column chromatography using 35 g silica gel. First, the unreacted acid chloride is eluted with chloroform, and the object substance is eluted with a 2%-methanol/chloroform mixture. The solvent of the object substance fraction is distilled off, and 2.35 g of 1-[$N^2$-(3-methyl-8-quinolinesulfonyl)-$N^G$-nitro-L-arginyl]-4-phenylpiperidine is obtained as an amorphous solid. Yield 83%.

(b) 2.35 g (4.14 mmoles) of the 1-[$N^2$-(3-methyl-8-quinolinesulfonyl)-$N^G$-nitro-L-arginyl]-4-phenylpiperidine is dissolved in a mixture of 150 ml methanol, 10 ml water and 1.2 g acetic acid, and 0.45 g palladium black is added to the mixture and thus hydrogenation is conducted for 40 hours at ordinary temperature under ordinary pressure. Thereafter, the catalyst is separated by filtration, and the solution is basified with a 2N sodium hydroxide aqueous solution to pH 10~11. The solvent is distilled off and an oily substance deposits and it gradually solidifies to crystals. They are collected by filtration, washed with water and dried. Thus 1.79 g of 1-[$N^2$-(3-methyl-1,2,3,4-tetrahydro-8-quinolinesulfonyl-L-arginyl]-4-phenylpiperidine is obtained as crystals. Yield 82%. m.p. 150°~153° C. IR(KBr): 3350, 1630, 1460 cm$^{-1}$.

EXAMPLE 5

(a) 2.85 g (0.00893 mole) of $N^2$-tert-butoxycarbonyl)-$N^G$-nitro-L-arginine and 0.90 g (0.00893 mole) of triethylamine are dissolved in 100 ml of tetrahydrofuran, and 1.22 g (0.00893 mole) of isobutyl chloroformate is added to the solution at $-25°~-20°$ C. After allowed to react for 30 minutes, a solution of 1.96 g (0.0089 mole) of optically active methyl 4-phenyl-2-piperidinecarboxylate (specific rotation $[\alpha]_D^{27}$ $-61.0°$ (C 0.66 MeOH)) dissolved in 5 ml tetrahydrofurane is added at $-25°~-20°$ C. over 15 minutes. The reaction is allowed to continue for 30 minutes at said temperature, and further for 1 hour at room temperature. Collection and purification by column chromatography are carried out in the same way as in Example 1 (a). By distilling off the solvent from the object substance fraction, 1.7 g of optically active methyl 1-[$N^2$-(tert-butoxycarbonyl)-$N^G$-nitro-L-arginyl]-4-phenyl-2-piperidinecarboxylate is obtained as an amorphous solid. Yield 37%.

(b) 1.7 g of the optically active methyl 1-[$N^2$-(tert-butoxycarbonyl)-$N^G$-nitro-L-arginyl]-4-phenyl-2-piperidinecarboxylate is dissolved in 7 ml of ethyl acetate, and 7 ml of a 20 w%-hydrogen chloride/ethyl acetate mixture is added to the solution under ice chilling. After 10 minutes, the reaction mixture is brought to room temperature and is stirred for 3 hours. Precipitate is formed and it is washed by adding 50 ml of ethyl ether and the supernatant is removed by decantation. After several times of washing with ethyl ether, the solvent is completely distilled off, and 1.59 g of white powder of optically active methyl 1-($N^G$-nitro-L-arginyl)-4-phenyl-2-piperidinecarboxylate is obtained. Yield 99%.

(c) 1.59 g (0.00325 mole) of the optically active methyl 1-($N^G$-nitro-L-arginyl)-4-phenyl-2-piperidinecarboxylate and 0.99 g (0.00978 mole) of triethylamine are dissolved in 50 ml of chloroform, and 1.0 g (0.00390 mole) of 4-methoxy-2-naphthalenesulfonyl chloride is added to the solution under ice chilling. The reaction is allowed to continue for 10 minutes at said temperature and further for 2 hours at room temperature. Collection and purification by column chromatography are carried out in the same way as in Example 1 (c). By distilling off the solvent from the object substance fraction, 1.69 g of optically active methyl 1-[$N^2$-(7-methoxy-2-naphthalenesulfonyl)-$N^G$-nitro-L-arginyl]-4-phenyl-2-piperidinecarboxylate is obtained as an amorphous solid. Yield 81%.

(d) 1.69 g of the optically active methyl 1-[$N^2$-(7-methoxy-2-naphthalenesulfonyl]-4-phenyl-2-piperidinecarboxylate is dissolved in a mixture of 30 ml tetrahydrofurane and 10 ml water, 4 ml of a 2N sodium hydroxide aqueous solution is added to the solution and the reaction is allowed to continue for 4 hours. Thereafter, the reaction mixture is acidified with 2N hydrochloric acid to pH 5~6 and the tetrahydrofurane is distilled off. When residue is further acidified with 2N hydrochloric acid to pH 1~2, an oily substance deposits and it crystalizes on standing. The crystals are collected by filtration and dried and thus 1.40 g of optically active 1-[N²-(7-methoxy-2-naphthalenesulfonyl)-N^G-nitro-L-arginyl]-4-phenyl-2-piperidinecarboxylic acid is obtained. Yield 85%. m.p. 116°~120° C.

(e) 1.40 g of the optically active 1-[N²-(7-methoxy-2-naphthalenesulfonyl)-N^G-nitro-L-arginyl]-4-phenyl-2-piperidinecarboxylic acid is dissolved in a mixture of 10 ml ethanol, 5 ml water and 1 ml acetic acid, hydrogenation is conducted by addition of 200 mg palladium black at room temperature under ordinary pressure. After 30 hours, the catalyst is removed by filtration, and the solvent is distilled off. The residue is dissolved in 20 ml water and is basified with a 2N sodium hydroxide aqueous solution to pH 10. Thus crystals deposit. They are collected by filtration and dried and 1.15 g of 1-[N 2-(7-methoxy-2-naphthalenesulfonyl)-L-arginyl]-4-phenyl-2-piperidinecarboxylic acid is obtained as crude crystals. By recrystallization from a water-ethanol mixture, 0.92 g of purified crystals are obtained. Yield 71%. m.p. 235°~239° C. Specific rotation $[\alpha]_D^{25}$ +41.2° (C 0.97 MeOH). IR(KBr): 3420, 1630, 1600 cm$^{-1}$.

Other arginine derivatives of this invention were synthesized in accordance with the processes described in the above Examples 1~5. The results are summarized in Table 1 together with the results of Examples 1~5.

Pharmacological Test

Trypsin-inhibiting activity of the arginine derivatives of this invention was determined by the method described below. The results are also summarized in Table 1.

Determination of Trypsin-Inhibiting Activity

Trypsin activity is determined by measuring the rate of formation of para-nitroaniline from synthesized chromogenic substrate Jz-Ile-Glu($\gamma$-OH and $\gamma$-OCH$_3$)-Gly-Arg-pNA (S-2222)(benzoylisoleucylglutamyl($\gamma$-OH:$\gamma$-OCH$_3$=1:1)glycylarginine p-nitroanilide) supplied by Kabi Diagnostica Inc. Three (3) ml of a reaction mixture containing 33.3 $\mu$M of S-2222 and 0.1 M Tris-HCl buffer solution (pH 8.3) is placed in a cell for spectrophotometry and the cell is placed in the thermostatic cell holder at 37° C. of a Hitachi 124 spectrophotometer. After the cell is kept at 37° C. for 3 minutes, 10 $\mu$l of a solution of trypsin dissolved in 0.001N HCl containing 0.05M CaCl$_2$ is added, and increase in absorbance at 405 nm is continuously measured using a recorder to calculate $\Delta$A/min at an initial portion. Various inhibitors in various concentrations are added and $\Delta$A/min values are respectively measured. Data are plotted with the inhibitor concentration as abscissa and $\Delta$A/min as ordinate. From the resulting graph the inhibitor concentrations which give $\Delta$A/min corresponding to 50% of the $\Delta$A/min value when no inhibitor is added are sought as I$_{50}$.

TABLE 1

| Run No. | Synthesis (Ex. No.) | Structure R¹ | R² | m.p. (°C.) | I$_{50}$ ($\mu$M) | IR(KBr) (cm$^{-1}$) |
|---|---|---|---|---|---|---|
| 1 (Ex. 4) | 4 | [CH₃-tetrahydroquinoline-SO₂–] | [–N(piperidine)-phenyl] | 150~153 (softens) | 2.1 | 3350, 1630 1460 |
| 2 (Ex. 1) | 1 | [CH₃O-naphthalene-SO₂–] | " | 217~220 (decomp.) | 0.23 | 3340, 1620 1450 |
| 3 | " | [CH₃O,CH₃O-naphthalene-SO₂–] | " | 233~236 (decomp.) | 2.4 | 3350, 1620 1500 |
| 4 | " | " | [–N(piperidine)-CH₂-phenyl] | 213~215 (decomp.) | 3.5 | 3350, 1625 1500 |
| 5 | " | [CH₃-phenyl-SO₂–] | [–N(piperidine)-phenyl] | 145~148 (softens) | 22 | 3325, 1620 1450 |
| 6 | " | [CH₃-tetrahydroquinoline-SO₂–] | [–N(piperazine)-N-phenyl] | 145~147 (decomp.) | 10 | 3350, 1630 1600 |

TABLE 1-continued

| Run No. | Synthesis (Ex. No.) | Structure R¹ | R² | m.p. (°C.) | $I_{50}$ (μM) | IR(KBr) (cm$^{-1}$) |
|---|---|---|---|---|---|---|
| 7 | 1 | CH₃O—[naphthalene]—SO₂— | —N[piperazine]N—[phenyl] | 231~234 (decomp.) | 1.5 | 3350, 1620 1600 |
| 8 | " | CH₃—[phenyl]—SO₂— | " | 234~226 (decomp.) | 74 | 3350, 1625 1600 |
| 9 | " | CH₃O,CH₃O—[naphthalene]—SO₂— | " | 231~234 | 7.8 | 3350, 1620 1595 |
| 10 | " | [dibenzofuran]—SO₂— | —N[piperidine]—[phenyl] | 219~221 | 2.2 | 3390, 1625 1465 |
| 11 | " | [fluorene]—SO₂— | " | 210~213 (decomp.) | 3.2 | 3350, 1625 1450 |
| 12 | " | CH₃—[naphthalene]—SO₂— | " | 219~222 | 1.0 | 3350, 1625 1450 |
| 13 | 1 | CH₃O,OCH₃—[naphthalene]—SO₂— | —N[piperidine]—[phenyl] | 157~159 (softens) | 2.25 | 3350, 1620 1460 |
| 14 | " | [naphthalene]—CO— | " | amorphous | 395 | 3300, 1620 1450 |
| 15 | " | O,O(—CH₂CH₂—)—[naphthalene]—SO₂— | " | 156~159 (softens) | 6.0 | 3350, 1625 1500 |
| 16 | 3 | CH₃O—[naphthalene]—SO₂— | —N[piperazine]N—[phenyl]—Cl (4-Cl) | 221~225 (decomp.) | 0.69 | 3340, 1620 1595 |
| 17 | " | " | —N[piperazine]N—[phenyl]—Cl (3-Cl) | 149~151 (softens) | 0.38 | 3340, 1620 1595 |
| 18 (Ex. 3) | " | " | —N[piperazine]N—[phenyl]—Cl (2-Cl) | 219~221 (decomp.) | 0.33 | 3330, 1625 1480 |

TABLE 1-continued

| Run No. | Synthesis (Ex. No.) | Structure R¹ | Structure R² | m.p. (°C.) | $I_{50}$ (μM) | IR(KBr) (cm⁻¹) |
|---|---|---|---|---|---|---|
| 19 | 1 | 2,4-dimethoxy-3-ethoxyphenyl-SO₂— (CH₃O, OCH₃, OC₂H₅ substituents) | —N(piperidine)-C₆H₅ (4-phenylpiperidine) | 148~151 (softens) | 2.4 | 3350, 1625 1450 |
| 20 | " | 6-methoxy-2-naphthyl-SO₂— | —N(piperazine)N-(2-methoxyphenyl) | 231~233 | 0.8 | 3350, 1630 1505 |
| 21 | " | 6-ethoxy-2-naphthyl-SO₂— | —N(piperidine)-C₆H₅ (4-phenylpiperidine) | 142~145 (softens) | 0.9 | 3350, 1620 1600 |
| 22 | " | 6-methoxy-2-naphthyl-SO₂— | —N(piperazine)N-(2-methylphenyl) | amorphous | 0.4 | 3350, 1620 1595 |
| 23* | 2 | " | —N(piperidine with COOC₂H₅)-C₆H₅ | " | 0.65 | 3350, 1725 1640, 1595 |
| 24 (Ex. 2) | " | " | —N(piperidine with COOH)-C₆H₅ | 182~186 (softens) | 0.4 | 3400, 1620 1595 |
| 25 | 1 | " | —N(piperidine)-CH₂-C₆H₅ | 163~166 | 0.6 | 3350, 1625 1450 |
| 26 | 3 | " | —N(piperazine)N-(4-fluorophenyl) | 167~170 (softens) | 0.86 | 3350, 1620 1505 |
| 27 | 1 | " | —N(piperidine with COCH₃ and C₆H₅) | amorphous | 35 | 3350, 1700 1625 |
| 28 | " | " | —N(piperazine)N-(4-methoxyphenyl) | 160~163 (softens) | 2.8 | 3350, 1620 1505 |
| 29 | " | 5-methoxy-1-naphthyl-SO₂— | —N(piperidine)-C₆H₅ (4-phenylpiperidine) | 203~206 (softens) | 2.2 | 3350, 1620 1455 |

TABLE 1-continued

| Run No. | Synthesis (Ex. No.) | Structure R¹ | R² | m.p. (°C.) | $I_{50}$ (μM) | IR(KBr) (cm⁻¹) |
|---|---|---|---|---|---|---|
| 30 | " | CH₃O-naphthyl-SO₂— (6-methoxy-2-naphthalenesulfonyl) | —N(piperidine)-C(CN)(phenyl)- (4-cyano-4-phenylpiperidine) | 223~225 | 1.3 | 3350, 2220 1620 |
| 31 | 1 | 6-methoxy (other isomer)-naphthyl-SO₂— | —N-piperidine-4-phenyl | 230~232 (decomp.) | 41.2 | 3350, 1620 1450 |
| 32 | " | 6,7-dimethyl-naphthyl-SO₂— | " | 217~219 (decomp.) | 9.0 | 3350, 1620 1450 |
| 33 | " | CH₃O-naphthyl-SO₂— | —N-piperidine-4-CONH-phenyl | 210~213 | 3.4 | 3380, 1660 1600 |
| 34 | " | 5,6,7,8-tetrahydronaphthalene-1-SO₂— | —N-piperidine-4-phenyl | 197~200 (decomp.) | 7.7 | 3380, 1630 1455 |
| 35 | " | 5,6,7,8-tetrahydronaphthalene-2-SO₂— | " | 230~232 (decomp.) | 6.7 | 3375, 1625 1450 |
| 36 | " | 8-methoxy-naphthalene-1-SO₂— | " | amorphous | 87 | 3350, 1640 1460 |
| 37 | 1 | naphthalene-1-SO₂— | " | 172~175 (decomp.) | 11 | 3400, 1620 1450 |
| 38 | " | naphthalene-2-SO₂— | " | 210~213 (softens) | 3.2 | 3380, 1630 1580 |
| 39 | " | CH₃O-naphthyl-SO₂— | —N-piperidine-4-(2-methoxyphenyl) | 215~225 (decomp.) | 0.28 | 3350, 1625 1460 |
| 40 | " | " | —N-piperidine-4-(2-methylphenyl) | 155~165 (decomp.) | 0.40 | 3350, 1625 1460 |

TABLE 1-continued
| Run No. | Synthesis (Ex. No.) | Structure R¹ | R² | m.p. (°C.) | $I_{50}$ (μM) | IR(KBr) (cm$^{-1}$) |
|---|---|---|---|---|---|---|
| 41 | 3 | " | 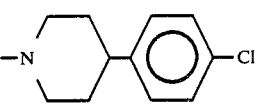 | 220~230 (decomp.) | 0.46 | 3350, 1620 1455 |
| 42 | 1 | 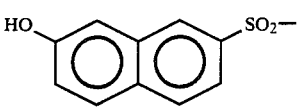 | 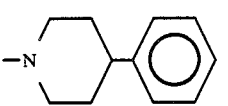 | 260~265 (decomp.) | 37 | 3450, 1635 1450 |
| 43 | " | 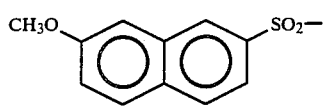 | 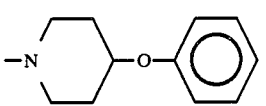 | 175~160 | 25 | 3400, 1630 1460 |
| 44 | " | 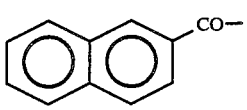 | 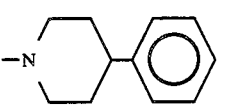 | amorphous | 110 | 3360, 1625 1540 |
| 45 | 3 | 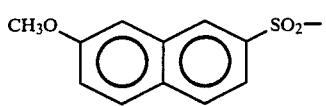 | 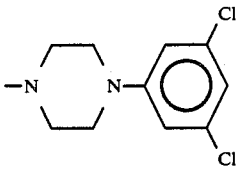 | 232~235 (decomp.) | 1.0 | 3400, 1625 1585 |
| 46 | 1 | " | 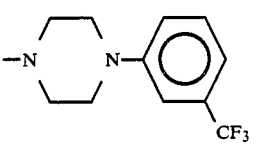 | 217~222 (decomp.) | 1.6 | 3400, 1625 1450 |
| 47 | 3 | 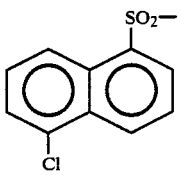 | 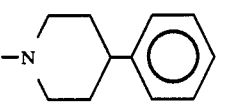 | 223~226 (decomp.) | 2.5 | 3400, 1625 1455 |
| 48 | " | 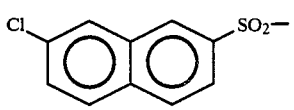 | " | amorphous | 1.1 | 3400, 1630 1450 |
| 49* | 1 | 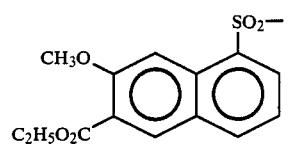 | 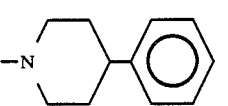 | amorphous | 2.1 | 3400, 1720 1625 |
| 50 | 2 | 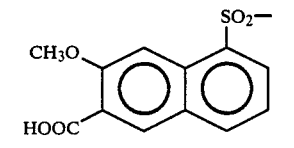 | " | 226~229 (softens) | 450 | 3400, 1630 1565 |
| 51 | 1 | 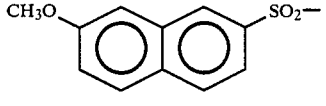 | 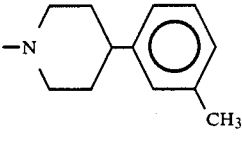 | 210~215 (decomp.) | 0.3 | 3400, 1625 1460 |

TABLE 1-continued

| Run No. | Synthesis (Ex. No.) | Structure R¹ | R² | m.p. (°C.) | I₅₀ (μM) | IR(KBr) (cm⁻¹) |
|---|---|---|---|---|---|---|
| 52 | " | " | 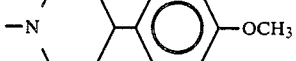 | 235~240 (decomp.) | 0.20 | 3350, 1625 1515 |
| 53 | " | " |  | 155~165 (softens) | 0.37 | 3420, 1625 1595 |
| 54* | 2 | 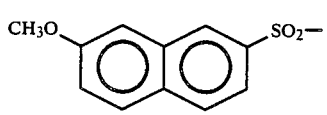 | 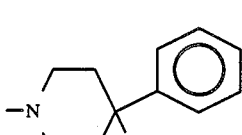 | amorphous | 12 | 3400, 1720 1635 |
| 55 | 1 | " | 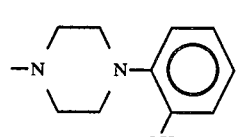 | 168~173 (decomp.) | 0.8 | 3400, 1625 1600 |
| 56 (Ex. 5) | 2 | " | 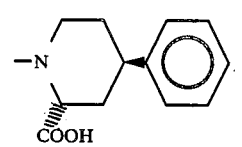 | 235~239 | 0.15 | 3400, 1625 1600 |
| 57 | " | " | 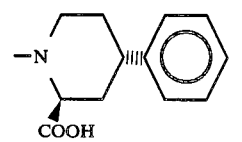 | 190~196 | 1.9 | 3400, 1630 1595 |
| 58 | 1 | " | 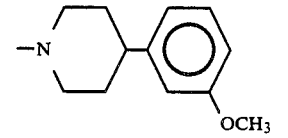 | 142~146 (softens) | 0.75 | 3350, 1620 1450 |

*Acetate

We claim:
1. An arginine compound of formula (I):

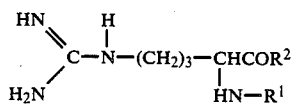

(I)

wherein R¹ stands for

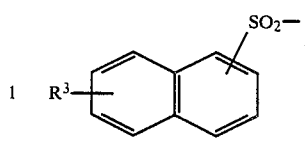

1 wherein R³ stands for CH₃O—, C₂H₅O— or CH₃—,

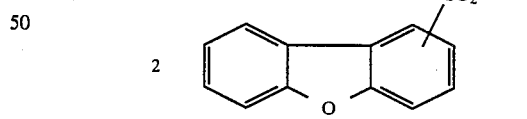

2 and R² stands for

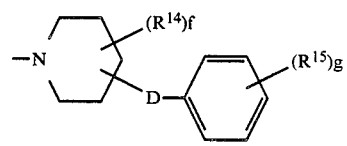

wherein R₁₄ stands for cyano group, and R₁₅ stands for hydroxyl group, cyano group halogen atom, C₁₋₆ alkyl group, C₁₋₆ alkoxyl group, C₂₋₆ acyl group, halogen-substituted C₁₋₆ alkyl group, carboxyl group or C₂₋₆ alkoxycarbonyl group, f is an integer of 0~4, g is an integer of 0~3, and D stands for —O—, —S—, —CONH— or —(CH₂)ₕ, wherein h is an integer of 0~4, and pharmaceutically acceptable acid addition salts thereof.

2. The arginine compound of claim 1, wherein $R^1$ stands for

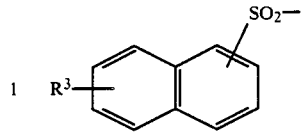

wherein $R^3$ stands for CH₃O—, C₂H₅O— or CH₃—,

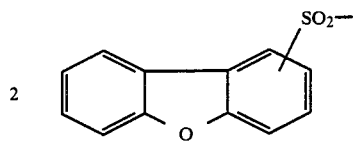

and $R^2$ stands for

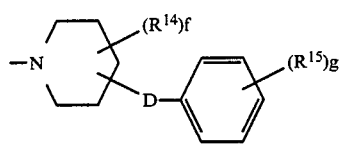

wherein $R^{14}$ stands for cyano group, and $R^{15}$ stands for halogen, C₁-C₆ alkyl group, C₁-C₆ alkoxy group, carboxyl group or C₂-C₆ alkoxycarbonyl group, f is 0 or 1, g is an integer of 0~2, and D stands for —O—, —CONH— or —(CH₂)ₕ—, wherein h is 0 or 1, and pharmaceutically acceptable acid addition salts thereof.

3. The arginine compound of claim 2, wherein $R^1$ stands for

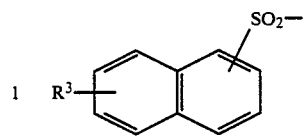

wherein $R^3$ stands for CH₃O—, C₂H₅O— or CH₃—,

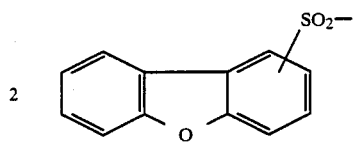

and $R^2$ stands for

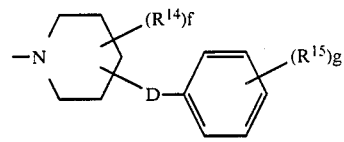

wherein $R^{14}$ stands for cyano group, and $R^{15}$ stands for halogen atom, C₁-C₄ alkyl group, C₁-C₄ alkoxy group, carboxyl group or C₂-C₄ alkoxycarbonyl group, f is 0 or 1, g is an integer of 0~2, and D stands for —O—, —CONH— or —(CH₂)ₕ—, wherein h is 0 or 1, and pharmaceutically acceptable acid addition salts thereof.

4. An arginine compound of formula (I):

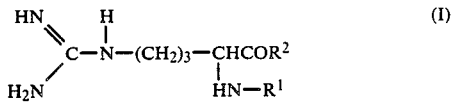

wherein $R^1$ stands for

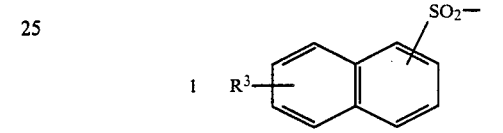

wherein $R^3$ stands for CH₃O—, C₂H₅O— or CH₃—,

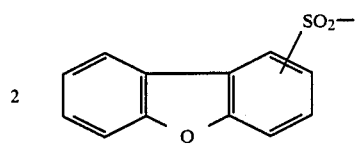

and $R^2$ stands for

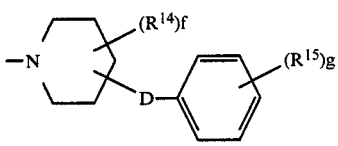

where $R^{14}$ stands for cyano group, and $R^{15}$ stands for hydroxyl group, cyano group, halogen atom, C₁₋₆ alkyl group, C₁₋₆ alkoxy group, C₂₋₆ acyl group, halogen-substituted C₁₋₆ alkyl group, carboxyl group or C₂₋₆ alkoxycarbonyl group, f is an integer of 0~4, g is an integer of 0~3, and D stands for —O—, —S—, —CONH— or —(CH₂)ₕ, wherein h is an integer 1~4, and pharmaceutically acceptable salts thereof.

* * * * *